USOO5762906A

United States Patent [19]
Creighton

[11] Patent Number: 5,762,906
[45] Date of Patent: Jun. 9, 1998

[54] FURTHER IMPROVEMENTS RELATING TO RADIOLABELLING OF PROTEINS

[75] Inventor: Andrew Malcolm Creighton, London, England

[73] Assignee: British Technology Group Ltd., London, England

[21] Appl. No.: 244,855

[22] PCT Filed: Dec. 15, 1992

[86] PCT No.: PCT/GB92/02322

§ 371 Date: Jun. 16, 1994

§ 102(e) Date: Jun. 16, 1994

[87] PCT Pub. No.: WO93/11796

PCT Pub. Date: Jun. 24, 1993

[30] Foreign Application Priority Data

Dec. 16, 1991 [GB] United Kingdom ............... 9126650

[51] Int. Cl.[6] .......................... A61K 51/00; A61M 36/14
[52] U.S. Cl. .................... 424/1.65; 424/1.77; 424/1.11; 424/1.69; 530/300
[58] Field of Search .......................... 530/350, 402, 530/403, 391.3, 391.5, 391.9, 328, 300, 324–330, 333, 334, 338; 424/1.77, 1.11, 1.65, 1.69, 9.1; 536/22.1

[56] References Cited

U.S. PATENT DOCUMENTS 5,459,240 10/1995 Foxwell et al. ..................... 530/328

FOREIGN PATENT DOCUMENTS

| 2 186 579 | 8/1987 | United Kingdom . |
| 2186579 | 8/1987 | United Kingdom . |
| 9011289 | 10/1990 | WIPO . |
| WO 90/11289 | 10/1990 | WIPO . |
| WO 91/01305 | 2/1991 | WIPO . |

OTHER PUBLICATIONS

Foxwell et al (1988), British Journal of Cancer, vol. 57, pp. 489–493 Conjugation of Monoclonal Antibodies to a Synthetic Peptide Substrate for Protein Kinase: A Method for Labeling Antibodies with 32p.

Sullivan and Wong (1991), Analytical Biochemistry, vol. 197, pp. 65–68. A Manual Sequencing Method for Identification of Phosphorylated Amino Acids in Phospho Peptides.

Carlsson et al (1978), Biochem. Journal, vol. 173, pp. 723–737. Protein Thiolation and Reversible Protein—Protein Conjugation.

Zuhay (1983), Biochemistry (Protein Structure and Function), pp. 3–7.

Bramson et al (1985), J. Biological Chemistry, vol. 260, No. 29, pp. 15452–15457, "The Use of N–methylated Peptides and Depsipeptides to Probe the Binding of Heptapeptide Substrates to Camp–Dependent Protein Kinase".

Thomas et al (1987), Biochemistry, vol. 26, pp. 4461–4466, "Role of Enzyme–Peptide Substrate Backbone Hydrogen Bonding in Determining Protein Kinase Substrate Specificties".

Chemical Abstracts vol. 113, No. 3, 16 Jul. 1990, Columbus, Ohio USA, #20373s; Jenkins et al "Meaurement of protein . . . ", p. 315.

Biological Abstracts, vol. 86, No. 7, 1988, Philadelphia, PA, USA, #71619. Foxwell et al, "Conjugation of monoclonal antibodies . . . ".

*Primary Examiner*—John Kight
*Assistant Examiner*—Dameron Jones
*Attorney, Agent, or Firm*—Nixon & Vanderhye

[57] ABSTRACT

A structurally modified protein is provided that will bind to a tumor-associated structure wherein the amino group in at least one basic amino acid in the binding protein is structurally modified to convert the amino group, —NH$_2$, to the grouping —NH—CO—X—NHR in which R is H or an amino protecting group and the grouping —CO—X—NHR is the residue of a peptide of the formula NHR—X—COOH capable of acting as a substrate for a phosphokinase.

14 Claims, 3 Drawing Sheets

FURTHER IMPROVEMENTS RELATING TO RADIOLABELLING OF PROTEINS

BACKGROUND OF THE INVENTION

This invention relates to improvements in the labelling of monoclonal antibodies and other proteins with $^{32}$P. The term "protein" as used herein includes polypeptides.

Radiation therapy, particularly using $^{32}$P, is of interest as a possible method of treatment of certain cancer conditions and it is therefore of interest to be able to label antibodies or other targeting molecules with $^{32}$P. However, the labelling of the antibody or similar targeting molecule must be done in such a way that the specificity of the antibody or similar targeting molecule is retained in a labelled molecule that has appropriate in vivo stability.

Our earlier Patent, GB-B-2,186,579, describes a system for modifying a protein that will bind with a tumour-associated structure comprising the introduction into the binding protein of a peptide region which is capable of acting as a substrate for a phosphokinase. The resulting modified binding protein can then be $^{32}$P labelled by reacting it with a $^{32}$P labelled gamma nucleotide triphosphate in the presence of a phosphokinase.

In accordance with the procedures described in our earlier Patent GB-B-2,186,579, the peptide region capable of acting as a substrate for a phosphokinase is introduced into the binding protein by using a hetero-bifunctional protein crosslinking agent. For example, the targeting molecule may be reacted with N-succinimidyl-3-(2-pyridyldithio) propionate (SPDP) followed by reduction with dithiothreitol. The reaction with SPDP introduces the dithiopropionyl group onto a side-chain amino group of a lysine residue in the targeting molecule while the subsequent reduction step converts the dithio grouping into a terminal thiol group. This terminal thiol group provides the reactive site for introduction of the substrate molecule.

In accordance with the procedure described in our earlier UK Patent, it is then necessary to activate the substrate molecule by reacting the N-terminus of the substrate molecule with a bridging molecule which in turn can be reacted with the terminal thiol group on the targeting molecule. For example, if the substrate molecule has an N-terminal leucine residue, its amino group can be reacted with an N-hydroxysuccinimidyl ester to give for example an iodoacetamide or a phenyl maleimide which can then react with the thiol group of the thiopropionamido residue introduced on the targeting molecule so that the substrate molecule becomes attached to the targeting molecule through a short bridging group including a thio link. If the substrate molecule has an N-terminal cysteine residue, then its thiol group can be reacted with succinimidyl-4-(p-maleimidophenyl)butyrate and the reaction product then reacted with the targeting molecule.

In the targeting molecule/substrate conjugates described in our earlier Patent, the substrate molecule is linked through its N-terminus by a short sulphur-containing bridge to the terminal amino group of the lysine residues of the targeting molecule. However, the procedure to bring about this conjugation is chemically complex involving the use of the hetero-bifunctional bridging molecules.

DESCRIPTION OF THE INVENTION

We have now found that it is possible to introduce a targeting molecule/substrate conjugate by much simpler synthetic methods involving conventional peptide chemistry to give a phosphorylatable conjugate in which the substrate molecule is directly bonded through its carboxy terminus through a peptide link to the targeting molecule and that the resulting targeting molecule/substrate conjugates hereinafter referred to as structurally-modified targeting proteins, structurally-modified proteins or targeting protein/substrate peptide conjugates, when labelled with $^{32}$P, give conjugates that are more effective in vivo as therapeutic reagents.

Accordingly, the present invention provides a structurally-modified protein that will bind to a tumour-associated structure wherein the amino group in at least one basic amino acid in the binding protein is structurally modified to convert the amino group —NH$_2$ to the grouping —NH—CO—X—NHR in which R is H or an amino protecting group and the grouping —CO—X—NHR is the residue of a peptide of the formula NHR—X—COOH capable of acting as a substrate for a phosphokinase.

In accordance with the present invention, the structurally modified proteins are prepared by conventional peptide synthesis wherein the terminal carboxy group of the substrate peptide is linked to the amino group on a basic amino acid, normally lysine, contained within the sequence of the targeting molecule to form an amide linkage. Such amide linkages can be formed, for example, by protecting the amino group at the N-terminus of the substrate peptide by an amino protecting group, activating the free carboxy group at the carboxy terminus of the substrate peptide and reacting the activated substrate peptide with the targeting molecule so that an amide bond is formed between the activated carboxy group of the substrate peptide and the amino group in the basic amino acid in the targeting protein.

In accordance with the present invention the substrate peptide becomes linked by its carboxy terminus through an amide bond to the amino terminus of one or more of the basic amino acid units in the targeting protein. Such basic amino acids will normally be lysine where the epsilon amino group is available for amide formation. The number of basic amino acids in the targeting molecule that will be linked to a substrate peptide will depend upon the degree of phosphorylation ultimately required in the therapeutic reagent. Where the targeting protein is rich in lysine residues, it is less important that all of the lysine residues react than it is for a targeting protein that is relatively poor in lysine residues but the relative proportion of reactants will normally be such that sufficient of the lysine residues in the targeting protein are reacted with the substrate peptide and that sufficient of the substrate peptide conjugated into the targeting protein are phosphorylated to give a $^{32}$P conjugate that will have a therapeutically effective effect available from an amount of $^{32}$P conjugate that can be conveniently administered.

One of the attractions of the present invention is the relative simplicity with which the substrate peptide can be built into the targeting protein, compared to the chemistry involved in the method described in our earlier Patent. For example, all that is necessary, in accordance with the present invention, is for the N-terminus of the substrate peptide to be protected, and this can conveniently be done earlier by acetylation during synthesis of the substrate peptides. The carboxy terminus of the substrate peptide is then activated for amide formation e.g. by reaction with N-hydroxysuccinimide to form the N-hydroxysuccinimide ester of the N-protected substrate peptide in the presence of a dehydrating agent such as those used in peptide bond formation, for example di-imides such as di-isopropyl carbo-diimide, and the solution containing the reaction product can then be reacted, without the need for isolation or purification directly with the targeting protein to form the amide bond between the targeting protein and the substrate peptide.

This amide bond formation can conveniently occur by bringing the reagents together in a borate buffer solution normally at a pH of at least 8, e.g. pH 8–10, preferably pH 9. The majority of the amide bond formation between the substrate peptide and targeting protein occurs within an hour or two but it is experimentally convenient to leave the reagents at ambient temperature, e.g. 15° to 20° C. for 8 to 24 hours to maximise amide bond formation.

A further attraction of the present simple synthesis is the possibility of preparing a stock of the activated ester of the N-protected substrate peptide which can be stored stably in the original reaction solution at below −10° C., e.g. at −18° C., for prolonged periods and simply brought back to room temperature when it is required for reaction with the targeting protein.

The targeting protein used in the present invention can be any one of those described in our earlier-mentioned British Patent. These will normally be monoclonal antibodies that will bind with a tumour-associated antigen, for example antigens associated with solid tumours with relatively poor blood supplies. Such solid tumours include those found in the colon, ovaries and lungs and monoclonal antibodies to such tumour-associated antigens are already known and have already been used as delivery vehicles for other anti-tumour agents.

More generally, the binding protein may be any protein that will bind with a tumour-associated protein or other tumour-associated structure such as a glycolipid or carbohydrate, where the tumour is one susceptible to high energy beta particles and, in addition to monoclonal antibodies, the targeting protein could be, for example, an Fab fragment of an antibody or a hormone or similar peptide that will bind to an appropriate receptor site identified on certain types of tumour cell, e.g. melanocyte-stimulating hormone, epithelial growth factor, interferons and mitogenic peptides such as bombesin.

For the purposes of an experimental demonstration of the benefits of the present invention, work is done with monoclonal antibodies usable in rat and mouse experimental systems.

The substrate peptides that can be used in the present invention are essentially the same as those used in the invention described in our above-mentioned British Patent. In the phosphorylation step, commercial availability of phosphokinases favours the use of serine or threonine kinases which in turn points to the use of substrate peptides containing serine and/or threonine residues. In general, serine-containing substrates phosphorylate relatively easily while threonine-containing substrates lead to products with relatively higher in vivo stability to phosphatases. Preferably then, the substrate peptide contains a threonine and/or serine residue and more preferably contains a threonine residue. Examples of such substrate peptides include the heptapeptide that has become known as Kemptide having the structure Leu.Arg.Arg.Ala.Ser.Leu.Gly SEQ ID NO: 1
or related peptides of the structure
Leu.Arg.Arg.Ala.Thr.Leu.Gly SEQ ID NO: 2
Arg.Arg.Arg.Arg.Pro.Ser.Pro.Ala SEQ ID NO: 3
Arg.Arg.Arg.Arg.Pro.Thr.Pro.Ala SEQ ID NO: 4
Leu.Arg.Arg.Ala.Ser.Leu.Gly.Ala SEQ ID NO: 5
Leu.Arg.Arg.Ala.Thr.Leu.Gly.Ala SEQ ID NO: 6
Lys.Tyr.Arg.Arg.Ala.Ser.Leu.Gly SEQ ID NO: 7
Cys.Arg.Arg.Lys.Ala.Ser.Gly.Pro.Pro.Val SEQ ID NO: 8
Leu.Arg.Arg.Ser.Leu.Gly.Ala SEQ ID NO: 9
Leu.Arg.Arg.Ser.Leu.Gly SEQ ID NO: 10
Leu.Arg.Arg.Thr.Leu.Gly SEQ ID NO: 11
Arg.Arg.Arg.Arg.Pro.Thr.Pro.Ala.Ala SEQ ID NO: 12
Arg.Arg.Arg.Arg.Pro.Thr.Val.Ala SEQ ID NO: 13

In the above peptides and all other peptides listed or referred to in this specification, the peptides read from left to right in the N-terminal to C-terminal direction.

It is necessary to protect the N-terminus of the substrate peptide during the reaction with the targeting protein. Protection by acetylation is the preferred method of protection since such acetyl groups are clinically acceptable and inert and it is not necessary to remove this protecting group either during the subsequent phosphorylation step or during the clinical use of the phosphorylated material. It is also introduced very conveniently during solid phase peptide synthesis after detachment of the protected peptide from the Merrifield resin and before removal of the other protecting groups. Since the terminal acetylamino group is so similar to a peptide bond, it is quite stable to the standard "deprotecting" procedures.

Once the substrate peptide has been introduced into the targeting protein, it can be phosphorylated or thiophosphorylated to introduce $^{32}$P. The phosphorylation can be carried out by procedures known per se and by procedures which are described in our earlier-mentioned British Patent. The phosphorylation is normally carried out by using gamma-$^{32}$P-adenosine triphosphate (gamma-$^{32}$P-ATP); or using gamma-$^{32}$P guanidine triphosphate, in the presence of a serine or threonine phosphokinase, e.g. a bovine heart protein kinase, which brings about the labelling with $^{32}$P of the serine or threonine residue in the substrate peptide. Although the serine-containing peptides can normally be phosphorylated very rapidly at 37° C., or more conveniently at room temperature, the threonine containing peptides usually require a longer time and it is necessary to reduce the temperature of the incubation to maintain the stability of the enzyme. Conveniently these labellings are carried out at 10° C. overnight although these conditions are not optimal. Alternatively, one of the commercially available tyrosine phosphokinases can be used in the presence of gamma-$^{32}$P-ATP to introduce $^{32}$P onto the tyrosine residue of the substrate peptide.

The phosphorylation of the substrate peptide portion of the structurally modified protein of the invention is normally carried out shortly prior to the clinical use of the labelled conjugate but the labelled conjugates are reasonably stable and can be stored prior to their clinical use.

Another synthetic alternative is to label the substrate peptide with $^{32}$P by treatment with, for example, gamma-$^{32}$P-ATP in the presence of the appropriate phosphokinase and then to bring about the conjugation of the labelled substrate peptide with the targeting protein by the methods described above. In this modification, attention must be paid to the possibility of reaction occurring between the activated substrate peptide and any basic amino groups that may be present in the phosphokinase.

As an alternative to phosphorylation, the structurally-modified targeting proteins of the invention can be thiophosphorylated by methods known per se, e.g. those disclosed in our WO90/11289.

The $^{32}$P labelled structurally-modified targeting proteins including the N-acetyl conjugates, are novel compounds, as are the unlabelled proteins and both the labelled and unlabelled proteins form part of the present invention.

Although unlabelled proteins of the present invention are designed primarily for $^{32}$P labelling by enzymatic methods, the conjugates are also available for $^{32}$P labelling by conventional chemical means.

Once the phosphorylation of the structurally-modified targeting proteins has been completed, the $^{32}$P labelled conjugate can be purified by standard chromatographic techniques such as gel filtration, e.g. on a Sephadex® column equilibrated with phosphate buffered saline. The $^{32}$P conjugate solution obtained in this way may then be filtered, e.g. using a 0.22 μm pore size filter so that it is in a suitable form for clinical use.

A further feature of the present invention provides a pharmaceutical composition, particularly one for parenteral administration, comprising a pharmaceutically acceptable diluent or carrier and the $^{32}$P-labelled structurally-modified targeting protein of the present invention.

Once a trace dose of the protein of the present invention is shown to target preferentially to a tumour region as compared to normal tissue, the labelled protein may then be administered intravenously or into various body regions for example by intraperitoneal, intrapleural or intra-arterial infusion.

The benefit of radiation treatment with $^{32}$P for certain types of cancer is already well established. The advantage of presenting the $^{32}$P source in one of the labelled proteins of the present invention is that it is possible to bring about a higher concentration of the labelled conjugate in the region of the tumour than appears to be possible by the use of the labelled conjugates of the type described in our earlier-mentioned British Patent and indeed, we have found that in certain instances, it is possible to make available 20% or more of the $^{32}$P-labelled material in the target area than is possible by the use of the $^{32}$P-labelled conjugates of the type described in our earlier-mentioned British Patent.

BRIEF DESCRIPTION OF THE DRAWINGS

The invention will now be described in more detail with reference to the accompanying drawings in which.

EXAMPLES

Figure 1A:
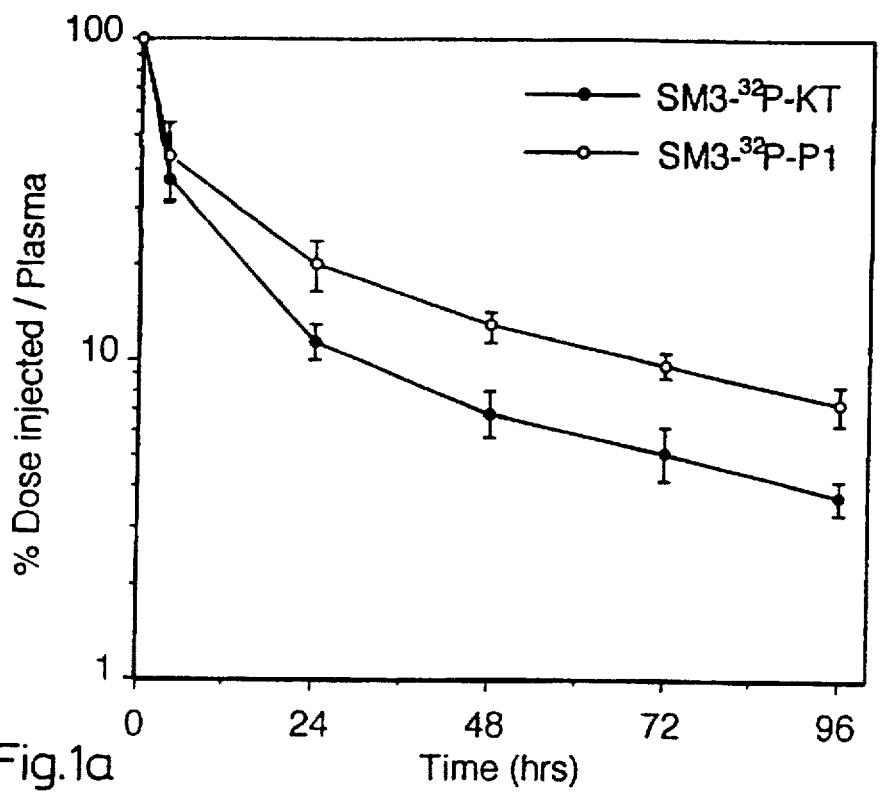
FIGS. 1A, 1B, 2A and 2B describe the results of experiments described in Example 4.

The following Examples are given to illustrate the present invention.

EXAMPLE I

Preparation of P1-peptide (CH$_3$ CO—NH—Leu.Arg.Arg.Ser.Leu.Gly.Ala)

This was prepared by conventional solid-phase peptide synthesis on an "Applied Biosystems 430A Peptide Synthesiser", the terminal acetyl group being added by treating the peptide with acetic anhydride after detachment from the resin but before cleaving the other protecting groups. The product showed essentially a single peak by HPLC analysis and the calculated molecular weight of 885 was confirmed by mass spectra.

Similarly prepared were:

CH$_3$CO—NH—Leu.Arg.Arg.Ser.Leu.Gly—Peptide 2

CH$_3$CO—NH—Leu.Arg.Arg.Thr.Leu.Gly—Peptide 3

CH$_3$CO—NH—Arg.Arg.Arg.Arg.Pro.Thr.Pro.Ala.Ala— Peptide 4 and

CH$_3$CO—NH—Arg.Arg.Arg.Arg.Pro.Thr.Pro.Val.Ala— Peptide 5 SEQ. ID NO: 14

EXAMPLE 2

Coupling of P1-peptide to the monoclonal antibody. SM3 to give SM3/P1 conjugate

The activated ester of the P1-peptide was prepared by adding a solution of N-hydroxysuccinimide [50 μl (5.65 μmoles) of a stock solution of 13.0 mg/ml in dry dimethylformamide (DMF)], followed by a solution of diisopropyl carbodiimide [50 μl (5.65 μmoles) of a stock solution of 17.4 μl/ml in dry DMF] to a solution of P1-peptide (5 mg, 5.65 μmoles) in dry DMF (250 μl). The reaction mixture was allowed to stand at about 20° C. overnight (ca. 18 hours) and then either used directly for conjugating to the antibody as described below or stored under anhydrous conditions at −18° C. for use later.

The solution of the activated ester of the peptide, prepared as above (20 μl), was added to 820 μl of a solution containing a monoclonal antibody SM3 (5.0 mg) that will target ovarian tumour tissue in borate buffer (0.05M sodium borate containing 0.1M sodium chloride and 0.5% v/v butan-1-ol; pH 9.0). A hybridoma producing SM3 was deposited in the European Collection of Animal Cell Cultures at Porton Down, Wiltshire, England, on 7th Jan. 1987 as Deposit No. ECACC-87010701. After incubation at about 20° C. for one hour, the reaction mixture was fractionated using a Pharmacia FPLC system. The sample was applied to a Superose 6 column, pre-equilibrated in the "enzyme buffer" [50 mM dipotassium hydrogen phosphate (pH 7.0) containing 5 mM magnesium chloride and 0.25 mM EGTA (ethyleneglycol-bis-β-aminoethyl-ether)-N,N,N'N'-tetraacetic acid)], and the protein, eluting as a single peak of molecular weight about 150,000 (about 4.5 mg (i.e. at least 90% yield) in 5 ml buffer) was filtered (0.22 μm) and stored at 4° C. The average number of P1-peptide groups conjugated to each antibody molecule by this procedure was known to be about 1.5 by trace-labelling a sample of the product with $^{32}$P.

SM3-P2, SM3-P3 and SM3-P5 conjugates were prepared in a similar manner from peptide 2, peptide 3 and peptide 5 respectively.

EXAMPLE 3

Phosphorylation of SM3-P1 conjugate

For high specific activity labelling, SM3-P1 stock solution (137 μl at 0.73 mg/ml, prepared as described in Example 2) and ×5 "enzyme buffer" (7 μl, 250 mM dipotassium hydrogen phosphate (pH 7.0) containing 25 mM magnesium chloride and 1.25 mM EGTA) was added to 1 mCi gamma of $^{32}$P-ATP (adenosine triphosphate) (20 μl, PB10218, Amersham International), followed by bovine heart protein kinase (10 μl, 50 U, Sigma). The reaction was incubated for 30 minutes at 37° C. and the protein was then desalted using a G50 'Sephadex' column (10 ml) equilibrated in phosphate-buffered saline which had been prewashed in phosphate-buffered saline containing bovine serum albumin (2 mg/ml). Under these conditions, about 0.03 phosphate moieties were incorporated into each molecule of SM3 with a specific activity of about 1.25 μCi/μg (42% yield). This labelled conjugate was designated SM3-$^{32}$P-P1. SM3-$^{32}$P-P2 was prepared in a similar manner giving a product of specific activity 1.37 μCi/μg (46% yield). For comparison purposes SM3 was coupled with Kemptide using SPDP using the procedure described in our above-mentioned British Patent and the conjugate labelled with $^{32}$P as described above to give SM3-$^{32}$P-KT having a specific activity of about 1.25 µCi/µg.

EXAMPLE 4

Rate of clearance of $^{32}$P-phosphorylated-SM3 from the blood

Figure 1B:
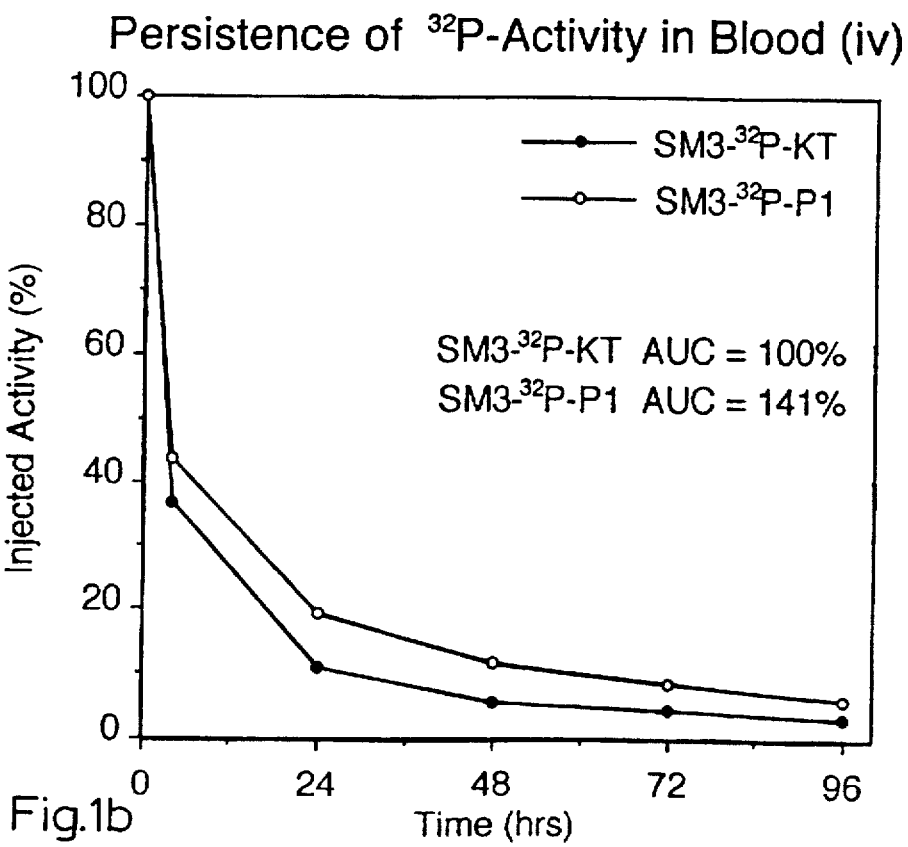
Figure 2A:
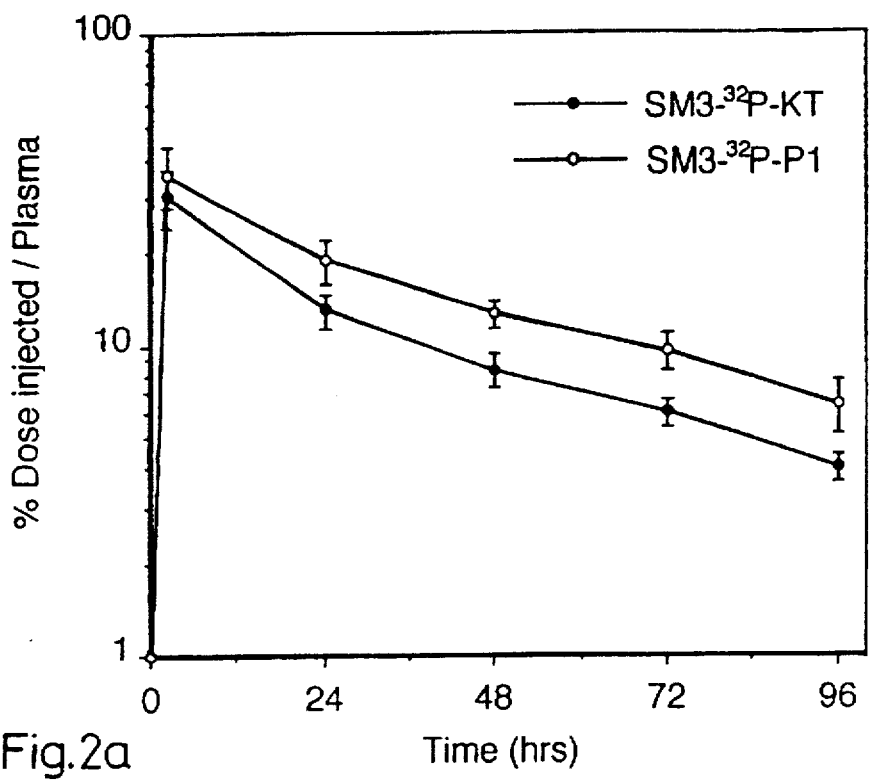
Figure 2B:
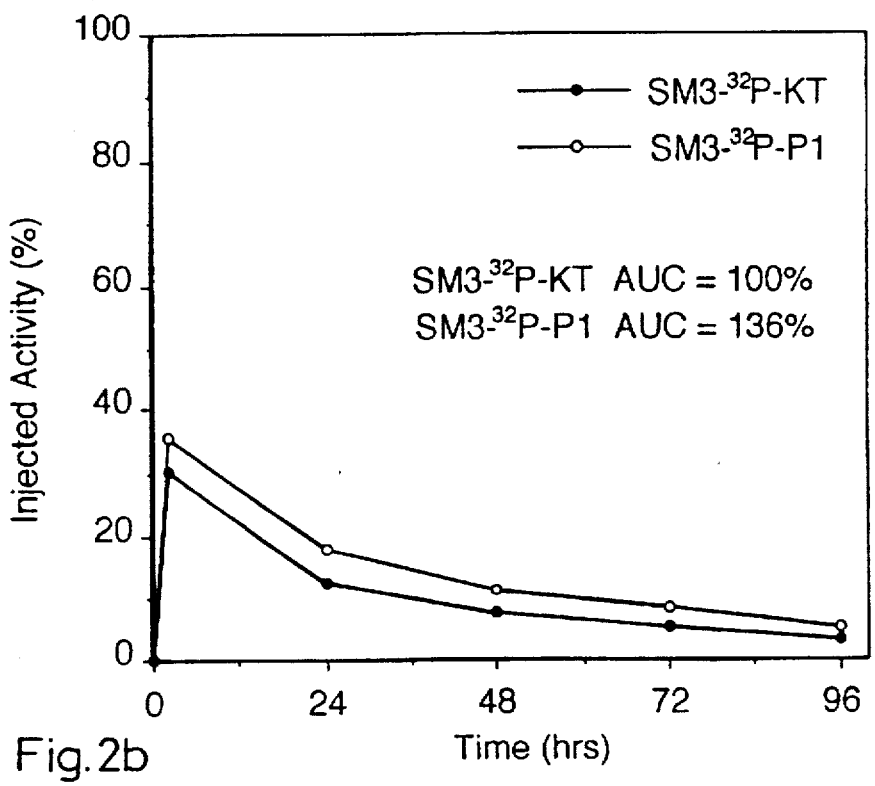

Balb/c mice (6–7/group) were injected (i.v.) with 5–10 µg of either SM3-$^{32}$P-P1 or SM3-$^{32}$P-KT. Blood samples were taken via the tail vein at various time points, the plasma separated and the acid-precipitable radioactivity counted. The rate of clearance of the radioactivity was demonstrably slower for the P1-peptide as indicated in FIG. 1a. If the same data is replotted on a linear scale and the radioactivity adjusted to allow for the decay due to the 14-day half-life, the persistence of $^{32}$P-activity in the blood can be shown to be 41% greater (AUC or area under the curve) with the P1-peptide than with the sulphide-linked KT peptide (FIG. 1b). Similar results were obtained with SM3 conjugates when administered by the intraperitoneal route and the results are illustrated in FIGS. 2a and 2b.

EXAMPLE 5

Phosphorylation of SM3-P3 and SM3-P5 conjugates

The phosphorylation of the SM3-P3 and SM3-P5 conjugates was carried out in a similar manner to Example 3 except that the incubation conditions were 24 hours at 10° C. and 26 hours at 10° C. respectively. These conditions, which were not optimal, gave SM3-$^{32}$P-P3 at 0.4 µCi/µg (19% yield) and SM3-$^{32}$P-P5 at 0.65 µCi/µg (18% yield).

EXAMPLE 6

Figure 3A:
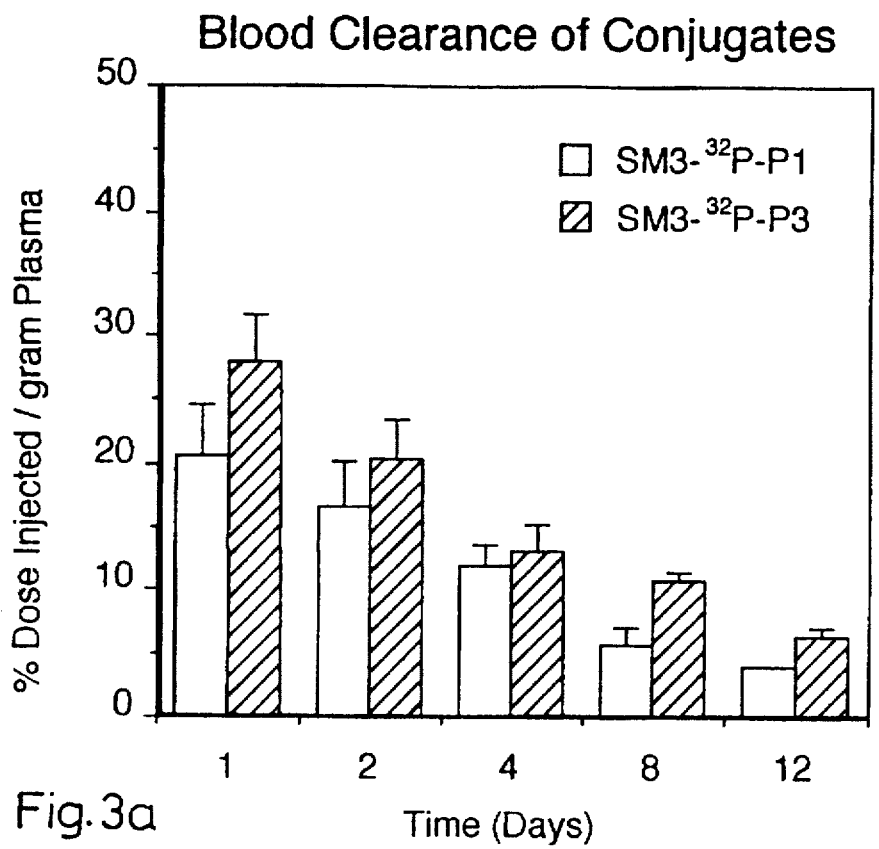
FIGS. 3A and 3B show the results of experiments described in Example 6
Figure 3B:
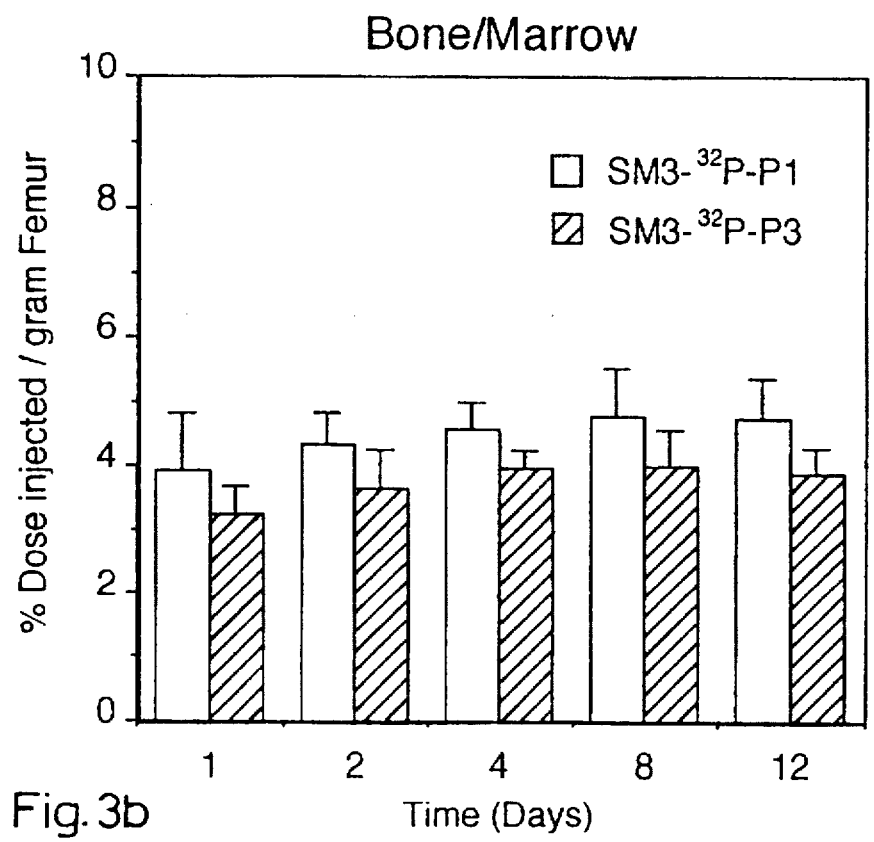

Rate of clearance of SM3-$^{32}$P-P1 and SM3-$^{32}$P-P3 from the blood and accumulation of $^{32}$P in bone/bone marrow Balb/c mice (groups of four) were injected (i.v.) with 5–10 µg each of either SM3-$^{32}$P-P1 or SM3-$^{32}$P-P3. At 1, 2, 4, 8 and 12 day intervals, the mice were killed using $CO_2$ and 1–2 ml of blood was removed, the plasma separated and the acid-precipitable radioactivity counted. The rate of clearance of the radioactivity was demonstrably slower for the P3-conjugate (FIG. 3a). Individual femurs were carefully removed, cleaned thoroughly externally while retaining the marrow, weighed, digested in methanolic KOH, and the radioactivity counted following neutralisation. The results showed relatively lower levels of the radioactivity from the P3, threonine-based, conjugate (FIG. 3b). The blood clearance and accumulation of $^{32}$P in the bone/bone marrow data together confirm the greater stability in vivo of the threonine-based conjugate.

I claim:

1. A structurally-modified protein that will bind to a tumor-associated structure, said protein being directly linked to a peptide capable of acting as a substrate for the phosphokinase, the linkage between said protein and said peptide substrate being an amide bond formed between the amino group of a basic amino acid present in said protein and the carboxyl group of said peptide substrate.

2. A structurally-modified protein according to claim 1, wherein at least one of the basic amino acids in said protein is lysine.

3. A structurally-modified protein according to claim 1, wherein said protein contains a serine and/or threonine residue.

4. A structurally-modified protein according to claim 3, wherein said protein contains a threonine residue.

5. A structurally-modified protein according to claim 1, wherein said protein contains the residue of the peptide Leu Arg Arg Ala Ser Leu Gly SEQ ID NO:1 or an amino protected derivative thereof.

6. A structurally-modified protein according to claim 1, wherein said protein contains the residue of the peptide Leu Arg Arg Ala Thr Leu Gly SEQ ID NO:2 or an amino protected derivative thereof.

7. A structurally-modified protein according to claim 1, wherein said protein contains the residue of the peptide Leu Arg Arg Ser Leu Gly Ala SEQ ID NO:9 or an amino protected derivative thereof.

8. A structurally-modified protein according to claim 1, wherein said protein contains the residue of the peptide Leu Arg Arg Ser Leu SEQ ID NO:15 or an amino protected derivative thereof.

9. A structurally-modified protein according to claim 1, wherein said protein contains the residue of the peptide Leu Arg Arg Thr Leu Gly SEQ ID NO:11 or an amino protected derivative thereof.

10. A structurally-modified protein according to claim 1, wherein said protein contains the residue of the peptide Arg Arg Arg Arg Pro Thr Pro Val Ala SEQ ID NO:14 or an amino protective derivative thereof.

11. A structurally-modified protein according to claim 1, wherein the amino group is protected by an acetyl group.

12. A structurally-modified protein according to claim 1, which is phosphorylated to introduce $^{32}P$.

13. A pharmaceutical composition comprising a structurally modified protein according to claim 1 and a pharmaceutically acceptable diluent or carrier.

14. A method for structurally modifying a protein that will bind to a tumor-associated structure which comprises forming an amide bond directly between the amino group of a basic amino acid present in a protein and the carboxyl group of a peptide capable of acting as a substrate for a phosphokinase.

* * * * *

SEQUENCE LISTING ( 1 ) GENERAL INFORMATION:

( i i i ) NUMBER OF SEQUENCES: 15

( 2 ) INFORMATION FOR SEQ ID NO:1:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:1:

Leu  Arg  Arg  Ala  Ser  Leu  Gly
    1                        5

( 2 ) INFORMATION FOR SEQ ID NO:2:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:2:

Leu  Arg  Arg  Ala  Thr  Leu  Gly
    1                        5

( 2 ) INFORMATION FOR SEQ ID NO:3:

( i ) SEQUENCE CHARACTERISTICS:
  ( A ) LENGTH: 8 amino acids
  ( B ) TYPE: amino acid
  ( C ) STRANDEDNESS: single
  ( D ) TOPOLOGY: linear ( i i ) MOLECULE TYPE: peptide ( x i ) SEQUENCE DESCRIPTION: SEQ ID NO:3:

Arg  Arg  Arg  Arg  Pro  Ser  Pro  Ala
1                        5

( 2 ) INFORMATION FOR SEQ ID NO:4:

( i ) SEQUENCE CHARACTERISTICS:
    ( A ) LENGTH: 8 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:4:

Arg  Arg  Arg  Arg  Pro  Thr  Pro  Ala
1                        5

( 2 ) INFORMATION FOR SEQ ID NO:5:

( i ) SEQUENCE CHARACTERISTICS:
    ( A ) LENGTH: 8 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:5:

Leu  Arg  Arg  Ala  Ser  Leu  Gly  Ala
1                        5

( 2 ) INFORMATION FOR SEQ ID NO:6:

( i ) SEQUENCE CHARACTERISTICS:
    ( A ) LENGTH: 8 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:6:

Leu  Arg  Arg  Ala  Thr  Leu  Gly  Ala
1                        5

( 2 ) INFORMATION FOR SEQ ID NO:7:

( i ) SEQUENCE CHARACTERISTICS:
    ( A ) LENGTH: 8 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:7:

Lys  Tyr  Arg  Arg  Ala  Ser  Leu  Gly
1                        5

( 2 ) INFORMATION FOR SEQ ID NO:8:

( i ) SEQUENCE CHARACTERISTICS:
    ( A ) LENGTH: 10 amino acids
    ( B ) TYPE: amino acid
    ( C ) STRANDEDNESS: single
    ( D ) TOPOLOGY: linear ( i i ) MOLECULE TYPE: peptide ( x i ) SEQUENCE DESCRIPTION: SEQ ID NO:8:

```
Cys  Arg  Arg  Lys  Ala  Ser  Gly  Pro  Pro  Val
 1                   5                        10
```

( 2 ) INFORMATION FOR SEQ ID NO:9:

( i ) SEQUENCE CHARACTERISTICS:
        ( A ) LENGTH: 7 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:9:

```
Leu  Arg  Arg  Ser  Leu  Gly  Ala
 1                   5
```

( 2 ) INFORMATION FOR SEQ ID NO:10:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:10:

```
Leu  Arg  Arg  Ser  Leu  Gly
 1                   5
```

( 2 ) INFORMATION FOR SEQ ID NO:11:

( i ) SEQUENCE CHARACTERISTICS:
        ( A ) LENGTH: 6 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:11:

```
Leu  Arg  Arg  Thr  Leu  Gly
 1                   5
```

( 2 ) INFORMATION FOR SEQ ID NO:12:

( i ) SEQUENCE CHARACTERISTICS:
        ( A ) LENGTH: 9 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:12:

```
Arg  Arg  Arg  Arg  Pro  Thr  Pro  Ala  Ala
 1                   5
```

( 2 ) INFORMATION FOR SEQ ID NO:13:

```
( i ) SEQUENCE CHARACTERISTICS:
        ( A ) LENGTH: 8 amino acids
        ( B ) TYPE: amino acid
        ( C ) STRANDEDNESS: single
        ( D ) TOPOLOGY: linear ( i i ) MOLECULE TYPE: peptide ( x i ) SEQUENCE DESCRIPTION: SEQ ID NO:13:

Arg Arg Arg Arg Pro Thr Val Ala
 1                5

( 2 ) INFORMATION FOR SEQ ID NO:14:

( i ) SEQUENCE CHARACTERISTICS:
            ( A ) LENGTH: 9 amino acids
            ( B ) TYPE: amino acid
            ( C ) STRANDEDNESS: single
            ( D ) TOPOLOGY: linear ( i i ) MOLECULE TYPE: peptide ( x i ) SEQUENCE DESCRIPTION: SEQ ID NO:14:

Arg Arg Arg Arg Pro Thr Pro Val Ala
 1                5

( 2 ) INFORMATION FOR SEQ ID NO:15:

( i ) SEQUENCE CHARACTERISTICS:
            ( A ) LENGTH: 5 amino acids
            ( B ) TYPE: amino acid
            ( D ) TOPOLOGY: linear ( i i ) MOLECULE TYPE: peptide ( x i ) SEQUENCE DESCRIPTION: SEQ ID NO:15:

Leu Arg Arg Ser Leu
 1            5
```